United States Patent
Westfall (10) Patent No.: US 7,418,963 B2
(45) Date of Patent: Sep. 2, 2008

(54) MOUTH-TO-MOUTH RESUSCITATOR DEVICE

(76) Inventor: Mark D. Westfall, 2413 Woodland Ter., Neenah, WI (US) 54956

(*) Notice: Subject to any disclaimer, the term of this patent is extended or adjusted under 35 U.S.C. 154(b) by 200 days.

(21) Appl. No.: 11/295,340

(22) Filed: Dec. 6, 2005

(65) Prior Publication Data
US 2007/0125373 A1    Jun. 7, 2007

(51) Int. Cl.
*A61M 16/00* (2006.01)
(52) U.S. Cl. ............................ 128/203.11; 128/202.28
(58) Field of Classification Search ............ 128/203.11, 128/202.28, 202.29, 205.24
See application file for complete search history.

(56) References Cited

U.S. PATENT DOCUMENTS

| | | | | |
|---|---|---|---|---|
| 3,303,845 | A | * | 2/1967 | Detmer, III ............ 128/202.28 |
| 4,819,627 | A | * | 4/1989 | Connors ................. 128/203.11 |
| 4,819,628 | A | | 4/1989 | Eisenberg et al. |
| 4,909,245 | A | | 3/1990 | Wollenhaupt |
| 4,991,575 | A | | 2/1991 | Fitz |
| 4,998,530 | A | | 3/1991 | DonMichael |
| 5,088,485 | A | | 2/1992 | Schock |
| 5,095,898 | A | | 3/1992 | Don Michael |
| 5,119,809 | A | | 6/1992 | Gerson |
| 5,127,397 | A | | 7/1992 | Kohnke |
| 5,165,396 | A | | 11/1992 | Don Michael et al. |
| 5,263,922 | A | | 11/1993 | Sova et al. |
| 5,355,877 | A | * | 10/1994 | Cheng ................... 128/203.11 |
| 5,388,570 | A | | 2/1995 | Wassil |
| 5,437,269 | A | | 8/1995 | Gooch |
| 5,465,712 | A | | 11/1995 | Malis et al. |
| 5,511,543 | A | * | 4/1996 | Shirley .................. 128/203.11 |
| 5,562,093 | A | | 10/1996 | Gerson |
| 5,664,559 | A | | 9/1997 | Baldwin |
| 5,765,551 | A | | 6/1998 | Sugino |
| 5,829,433 | A | | 11/1998 | Shigematsu et al. |
| 6,070,574 | A | * | 6/2000 | O'Day et al. .......... 128/203.11 |
| 6,209,537 | B1 | | 4/2001 | Baldwin |
| 6,405,726 | B1 | | 6/2002 | Baldwin |
| 6,691,703 | B2 | | 2/2004 | McKinney et al. |
| 2002/0007832 | A1 | | 1/2002 | Doherty |
| 2002/0008047 | A1 | | 1/2002 | Hammond |
| 2002/0020414 | A1 | | 2/2002 | Fukunaga |
| 2002/0024888 | A1 | | 2/2002 | Schreiber |
| 2002/0026229 | A1 | | 2/2002 | Weil et al. |
| 2002/0043263 | A1 | | 4/2002 | Baldwin |
| 2002/0069878 | A1 | | 6/2002 | Lurie et al. |
| 2002/0100475 | A1 | | 8/2002 | McKinney et al. |

(Continued)

*Primary Examiner*—Steven O Douglas
(74) *Attorney, Agent, or Firm*—Quarles & Brady LLP (57) ABSTRACT

A mouth to mouth resuscitator device for use by a rescuer for resuscitating a victim, the device comprising a sheet of flexible material having a top surface and an undersurface, the sheet forming a mouth opening, a hollow substantially rigid tube having an external surface, a first end, a second end and a tube length between the first and second ends, a tube passage aligned at least in part with the mouth opening, the tube extending from the undersurface of the sheet to the second end and a self closing one-way valve located within the tube passage to restrict flow from the second end to the first end of the tube and to allow flow from the first end to the second end when a rescuer exhales air into the mouth opening, wherein the external surface of the tube forms at least one recess at a location along the tube length, the recess for receiving a victim's teeth.

22 Claims, 9 Drawing Sheets

U.S. PATENT DOCUMENTS

| | | |
|---|---|---|
| 2002/0104774 A1 | 8/2002 | Hammond |
| 2002/0139369 A1 | 10/2002 | Maguire |
| 2004/0173213 A1 | 9/2004 | Maguire |
| 2005/0080360 A1 | 4/2005 | Katz et al. |
| 2005/0080361 A1 | 4/2005 | Escudero et al. |

* cited by examiner

MOUTH-TO-MOUTH RESUSCITATOR DEVICE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates generally to devices for providing mouth-to-mouth resuscitation or insufflation, and more specifically relates to devices having a physical barrier or shield between the mouth of the rescuer and the victim when providing mouth-to-mouth resuscitation to victims of suffocation, asphyxiation, cardiac arrest, drowning and the like.

Mouth-to-mouth resuscitation is a first aid technique and a preferred method for reviving a non-breathing victim, when life or death may be determined from actions taken within seconds, by rapidly delivering large volumes of exhaled air under pressure to inflate the lungs and reactivate the normal breathing process. In this method, the victim is placed on his or her back, the mouth is opened to check and clear any airway obstruction and making sure the tongue is not lodged in the passageway to be used and is positioned in the lower cavity inside the mouth, the chin is pulled forward, the head is tilted backward, the nose or nostrils are pinched closed, then an air tight seal is made with the lips of the rescuer and the victim, and the rescuer commences to evenly exhale a deep breath under pressure into the victim's mouth; and then the lip seal is broken to enable another deep breath to be taken and the nose air pathways are opened in the event of any exhaling by the victim; and the process is repeated, until hopefully, the victim is able to exhale and to finally inhale unaided by the rescuer.

In the past, possible rescuers were reluctant to engage in mouth-to-mouth resuscitation for fear of contracting disease or illness from such contact with the victim. Generally, however, the person would assume the risk when there was no other alternative for saving the life of the victim. The individual attitude is considerably different today, for there is a mortal fear, which may or may not have any basis in fact, that any close or intimate contact could result in being stricken with the acquired immune deficiency syndrome ("AIDS") virus, particularly if the victim is suspected of being a drug user or a homosexual. Presently there is no known cure and only certain death after a person contracts the AIDS virus, and the number of reported AIDS cases are dramatically increasing throughout the world. In view of this, people will avoid or just refuse to give mouth-to-mouth resuscitation without any safeguard for shielding against direct and intimate contact. The subject invention provides such protection for the person giving mouth-to-mouth resuscitation or practicing this technique.

Various devices have been devised to shield the rescuer when applying mouth-to-mouth resuscitation. For example, U.S. Pat. No. 3,802,428 (1974), Sherman, discloses a mouth-to-mouth resuscitator comprising a flexible face mask having a central opening formed therein and extends over the mouth area of the person administering artificial respiration. A flexible tubular member is attached to the periphery of the central opening and depends therefrom for placement in the mouth of the victim. The tubular member acts as a one way valve and inflates when delivering air and collapses for preventing any air or fluid flow in the reverse direction.

In Sherman there is no immediate closure action of the air pathway through the valve, and moist air or fluids from the victim could flow or seep back to the rescuer. Moreover, the face mask of this device could sufficiently contact the mouth and nose to partially or fully prevent the victim from exhaling.

U.S. Pat. No. 4,050,457 (1977), Davidson, utilizes a face shield having a central mouth opening formed therein. The shield conforms to the contours of the face in the mouth and nose area, and particularly provides a covering over the patient's lips to permit mouth-to-mouth resuscitation without intimate contact. However, moist air and/or fluids from the victim could still be transferred to the rescuer.

None of the aforesaid Patents provide a resuscitator device having a one way valve which instantly closes after air is delivered to the victim, to prevent any back flow of air or liquid from the victim to the rescuer, and includes means for ensuring that the victim is not inhibited from exhaling.

Furthermore, these and other resuscitator devices often include a stiff tube that is inserted into the victim's mouth to create a route for airflow to pass from the rescuer to the victim. These tubes extend into the victim's mouth to ensure that the victim's upper and lower teeth remain separated. However, there is a conflict between the size of the tube to ensure enough air passes from the rescuer to the victim, that the tube remains in place, and the pressure the tube exerts on the victim's teeth. None of the prior patents provide a guard for the victim's teeth.

Furthermore, resuscitator devices are designed to prevent the spread of diseases from the one of the rescuer and the victim and the other. However, when the rescuer performs mount-to-mouth resuscitation in a patient, the rescuer must firmly press his lips to the patient's lips, albeit with an intermediate shield separating them, so as to create a tight seal and prevent air from leaking from the victim's mount and not entering the victim's lungs.

When performing mouth-to-mouth resuscitation, there is always a chance that the victim may recover and move violently or have an uncontrolled muscle reflex. This presents a hazard to the rescuer and the victim as their teeth are in close and unprotected proximity to each other. This presents the potential for the rescuer or victim to chip or break a tooth if there is sufficient force or movement exerted by the victim. None of the prior patents provide a guard between the victim's teeth and the rescuer's teeth to protect them from injury.

SUMMARY OF THE INVENTION

The resuscitator device of this invention provides a physical shield between the rescuer and victim requiring mouth-to-mouth resuscitation. The device comprises a flexible sheet to conform to the contour of the face in the area of the mouth and nose. A mouth opening is formed centrally in the sheet. A rigid tube is bonded around the periphery of the mouth opening and depends downward therefrom to an output end. A self closing one way valve is positioned in the tube and includes a flexible sleeve having an open air inlet adjacent the mouth opening and an air outlet adjacent the output end of the tube. A spring strip is attached to the sleeve adjacent to the air outlet for tightly closing the air outlet.

The tube with the valve therein is inserted into the mouth of the victim and the sheet covers the mouth and nose area. The rescuer takes a deep breath and then makes a tight air seal around the mouth opening upon forcing his or her lips against the lips of the victim with the sheet sandwiched therebetween, and the deep breath is exhaled under pressure into the air valve via the mouth opening in the sheet. The forced air entering the valve spreads the sleeve walls apart and causes the spring strip to bow outwardly, for opening the valve and discharging the deep breath from the output end of the tube and into the mouth and lungs of the victim. The rigidity of the tube protects the valve and directs the forced air into the lungs.

After the exhaled deep breath has passed through the valve, the spring strip resiliently pulls the valve outlet closed, thereby instantly preventing any back flow of air, mist or liquid from the victim to the rescuer.

The resuscitator device herein is also suitable for use by the student or in a demonstration or practice with a manikin or another student for learning or practicing life saving techniques, particularly C.P.R. By each student having his or her own device a sanitary shield is thereby provided, which enables the same manikin to be continuously used without fear of contracting diseases.

The plastic materials which are preferred for use in the construction of the subject resuscitator device may have a tendency to cling. In view of this, the device herein includes safeguards for overcoming any clinging problem which could affect its life saving operation. Therefore, ribs protrude inward from the inside surface of the tube to prevent the valve walls from clinging to the inside tube surface. Furthermore, a rough surfaced patch is constructed in the bottom or victim's side of the flexible sheet, which is operatively located adjacent the nose. The rough surface, which may comprise a plurality of spaced apart bumps, prevents the sheet barrier from sticking to the nose and blocking air flow out from the victim's nose.

Moreover, grooves are formed in the bottom or victim's side of the sheet and extend from adjacent the mouth opening to the outer edges of the sheet. Hence, if the sheet barrier tightly clings to the lips of the victim, even after the rescuer has removed the pressure he or she has been applying thereto when delivering forced air to the victim, any air exhaled from the victim's mouth could flow to the outside through these grooves.

The tube can furthermore include one or more channels cut along its elongate length. The channel allows air and other material in the victim's mouth to be expelled without having to remove the tube and reduce the tendency of any air exhaled by the patient to push the tube and sheet out from their mouth. When the tube has an oval sectional shape along the elongated length, the channels can be formed at the narrow ends of the oval, corresponding when inserted in the victim to the corners of their mouth.

When the channel fits in the corner of the victim's mouth it is naturally kept open even when the victim's lips surround the tube. The victim's lips will generally not clog the channel allowing free communication from the interior of the mouth to the bottom side of the sheet. The grooves on the underside of the flexible sheet allow air to be exhausted from the victim's mouth. The channel can be enclosed or open running along the length of the tube. When enclosed, the channel will have an opening within the victim's mouth and another opening just below the flexible sheet allowing communication of air between the mouth and the underside of the flexible sheet.

In order to protect the victim's teeth, the tube can have an oval or oblong cross sectional shape with a recess provided along the tube for the victim's teeth to fit within. This recess extends across the oval section and is placed a suitable distance below the sheet, so as to match the typical distance between a victim's lips and teeth. When the tube is inserted in the victim's mouth their teeth will then rest in the recess, allowing a still unimpeded air flow from the rescuer and the victim, yet allowing the victim's teeth and jaw to assume a more natural position.

Additionally, the resuscitator device can have a teeth guard formed of a soft, pliable plastic or other material (for example a closed cell rubber like Neoprene®, urethane, or a co-injected plastic of a low durometer) formed around the tube on the opposite end that is placed in the victim's mouth. Unlike the sheet, the teeth guard has a substantial thickness to reduce the potential of shock or force caused by movement of the victim, for example it can be over ¼" in thickness. The teeth guard is designed to allow the rescuer's lips to pass around it so they can still make a tight seal with their lips against the sheet and the victim's lips and checks. However the teeth guard prevents the victim's teeth from making forceful contact with the rescuer's teeth. Should the patient suddenly move while the rescuer is giving mouth-to-mouth resuscitation, the teeth guard protects the rescuer's and the victim's teeth from damage. The guard provides increased safety than offered by a thin flexible sheet between the victim and rescuer's faces and teeth.

In some cases the entire sheet can be a teeth guard when it is made from a sheet of shock absorbing material, for example over ¼" of a soft durometer plastic. In this case a tight air seal can still be created between the patient lips and the sheet by the rescuer pressing their lips to the sheet, but now both the rescuer and the victim are protected by the sheet acting as a teeth guard.

It is also anticipated the teeth guard can be placed on the victim side of the sheet. For example it can take the form of an annular shape around the tube formed below the sheet so the patient's lips are in contact with the sheet and the teeth guard is positioned between the inner lip surface and the teeth.

It should be noted that in standard mouth-to-mouth resuscitation the heads of the rescuer and the victim are generally perpendicular to each other. A resuscitator device can have a tube shaped as an oval that is placed so the elongated side of the oval is positioned along the length of the victim's teeth. However the shape of this tube is naturally at a right angle to the mouth of the rescuer. The rescuer is then to place their lips so they completely cover the opening of the tube and press against the flexible sheet to form an air seal around the tube and the victim's mouth. The rescuer must open their mouth sufficiently so the upper and lower edges of their mouth cover the corners of the victim's mouth.

To assist the rescuer in properly placing their lips in the correct position, a teeth guard can be rounded so that, when the rescuer's lips are placed around the guard, the rescuers lips will be properly positioned with upper and lower lips covering the victim's mouth to properly ensure that a good air seal is formed. To provide improved protection for the teeth of the rescuer and the victim, the teeth guard should provide as much protection between the front teeth of the victim and the rescuer. For example the tube can project above the flexible sheet and rotate in shape with the teeth guard surrounding and projecting away from it. In one instance the tube forms that oval section that is oriented approximately 90 degrees to the victim's mouth so as to be aligned with the rescuer's mouth. It is also anticipated that the tube may form a circular shape forcing the rescuer's teeth to be positioned away from the victim's teeth.

At least some inventive embodiments include a mouth to mouth resuscitator device for use by a rescuer for resuscitating a victim, the device comprising a sheet of flexible material having a top surface and an undersurface, the sheet forming a mouth opening, a hollow substantially rigid tube having an external surface, a first end, a second end and a tube length between the first and second ends, a tube passage aligned at least in part with the mouth opening, the tube extending from the undersurface of the sheet to the second end and a self closing one-way valve located within the tube passage to restrict flow from the second end to the first end of the tube and to allow flow from the first end to the second end when a rescuer exhales air into the mouth opening, wherein the external surface of the tube forms at least one recess at a location along the tube length, the recess for receiving a victim's teeth.

In some cases the at least one recess extends substantially perpendicular to the tube length. In some cases the recess is formed substantially midway along the length of the tube. In some cases the tube forms a second recess, the first and second recesses are formed in opposite sides of the external surface of the tube and the first and second recesses are both formed substantially midway along the length of the tube. In some cases the tube has a substantially oval cross section with the external surface having oppositely facing long curved first and second sides and wherein the at least one recess is formed in the first side and extends substantially perpendicular to the tube length. In some cases the external surface also forms a second recess in the second side that is substantially aligned with the first recess.

In some cases the first and second recesses are spaced apart from the undersurface of the sheet. In some cases the recess has a bottom edge and the bottom edge is at least ¼" below the undersurface of the sheet. In some cases the first end of the tube is proximate and substantially flush with the top surface of the sheet. In some cases the tube extends through the sheet with the first end spaced apart from the top surface of the sheet so that a portion of the external surface is on the top surface side of the sheet.

In some cases the device further includes at least one resilient and flexible guard member supported by at least one of the portion of the external surface that is on the top surface side of the sheet and the sheet. In some cases the guard member is supported by the portion of the external surface that is on the top surface side of the sheet.

In addition, some embodiments include a mouth to mouth resuscitator device for use by a rescuer for resuscitating a victim, the device comprising a sheet of flexible material having a top surface and an undersurface, the sheet forming a mouth opening, a hollow substantially rigid tube having an external surface, a first end, a second end and a tube length between the first and second ends, a tube passage aligned at least in part with the mouth opening, the tube extending from the undersurface of the sheet to the second end, a self closing one-way valve located within the tube passage to restrict flow from the second end to the first end of the tube and to allow flow from the first end to the second end when a rescuer exhales air into the mouth opening and at least a first resilient and flexible tooth guard member that surrounds at least a portion of the mouth opening on the top surface side of the sheet, the at least one guard member supported by at least one of a portion of the tube and the sheet for absorbing force.

In some cases the wherein the guard member is supported by a portion of the external surface of the tube. In some cases the tube extends through the sheet to the first end that is spaced apart from the top surface and wherein the at least one guard member surrounds the external surface of the tube adjacent the first end of the tube. In some cases the at least one guard member contacts the top surface of the sheet and includes a surface that is substantially flush with the first end of the tube. In some cases the at least one guard member has a thickness between the top surface of the sheet and the surface that is substantially flush with the first end of the tube that is at least ¼th of an inch. In some cases the guard member is spaced apart form the top surface of the sheet. In some cases the separation between the top surface of the sheet and the guard member is at least ¼th of an inch.

In some cases the first end of the tube is substantially oval in cross section. In some cases the device is positionable with the second end in the victim's mouth and the sheet coving a portion of the victim's face such that when the rescuer's lips surround the at least one guard member with the guard member positioned between the rescuer's teeth and the sheet, as the rescuer's lips are pressed against the sheet, an air seal is created between the device and the victim. In some cases the mouth opening is oval shaped and the external surface of the tube proximate the undersurface of the sheet is substantially oval in cross section to force the lips and teeth of the victim slightly apart thereby enabling the lips of the rescuer to easily make a tight air seal with the victim's mouth when the sheet is therebetween.

Moreover, some embodiments include q mouth to mouth resuscitator device for use by a rescuer for resuscitating a victim, the device comprising a sheet of flexible material having a top side for contacting the rescuer and a bottom side for contacting the victim, the sheet forming a mouth opening, a hollow substantially rigid tube having an external surface, a first end, a second end and a tube length between the first and second ends, a tube passage aligned at least in part with the mouth opening, the tube extending from the undersurface of the sheet to the second end, a self closing one-way valve located within the tube passage to restrict flow from the second end to the first end of the tube and to allow flow from the first end to the second end when a rescuer exhales air into the mouth opening and a first channel supported by at least one of the tube and the sheet that extends along at least a portion of the tube length, the channel having first and second channel ends, the first end of the channel opening on the undersurface side of the sheet and the second end of the channel proximate the second end of the tube.

In some cases the external surface of the tube is oblong in cross section having first and second oppositely facing side walls at opposite ends of a wide dimension and wherein the tube forms the first channel in the first side wall. In some cases the tube further forms a second channel in the second side wall. In some cases when the second end of the tube is in a victim's mount, the second end of the channel is in the victim's mount. In some cases the undersurface of the sheet forms at least one air groove extending from adjacent the mouth opening to an outer edge of the sheet and wherein the second end of the channel opens into the at least one groove. In some cases the channel is closed along at least a portion of a channel length between the first and second channel ends.

Some embodiments include a mouth to mouth resuscitator device for use by a rescuer for resuscitating a victim, the device comprising a sheet of flexible material having a top side for contacting the rescuer and a bottom side for contacting the victim, the sheet forming a mouth opening, a hollow substantially rigid tube having an external surface, a first end, a second end and a tube length between the first and second ends, a tube passage aligned at least in part with the mouth opening, the tube including a first tube portion extending from the top surface to the first end and a second tube portion extending from the undersurface of the sheet to the second end where the first and second ends are spaced apart from the top and undersurfaces of the sheet, respectively; and a self closing one-way valve located within the tube passage to restrict flow from the second end to the first end of the tube and to allow flow from the first end to the second end when a rescuer exhales air into the mouth opening.

In some cases the first tube section is oblong in cross section perpendicular to the tube length and has a first wide cross sectional dimension and the second tube section is oblong in cross section perpendicular to the tube length and has a second wide cross sectional dimension and wherein the first and second wide dimensions are misaligned. In some cases the misalignment is at least 45 degrees. In some cases the misalignment is 90 degrees. In some cases each of the first and second tube portions have oval cross sectional shapes. In some cases the device further included at least one resilient and flexible guard member supported by and that at least in part surrounds a portion of the external surface of the first tube portion. In some cases the at least one of the first and second tube portions is connected to the sheet to rotate around the mouth opening about a mouth opening axis that is substantially perpendicular to the portion of the sheet adjacent the mouth opening.

BRIEF DESCRIPTION OF THE DRAWING

Referring to the drawing in which the same characters of references are employed to indicate corresponding similar parts throughout the several figures of the drawing.

DESCRIPTION OF THE PREFERRED EMBODIMENT

Referring now to the various Figures of the drawing, the reference numeral 10 indicates generally a resuscitator device for use as a physical barrier between a rescuer and a victim or patient when utilizing a procedure for resuscitating the patient, and is particularly suitable when engaging in Cardiac, Pulmonary Resuscitation (C.P.R.), or in other situations when the victim is unable or has extreme difficulty breathing.

Figure 1:
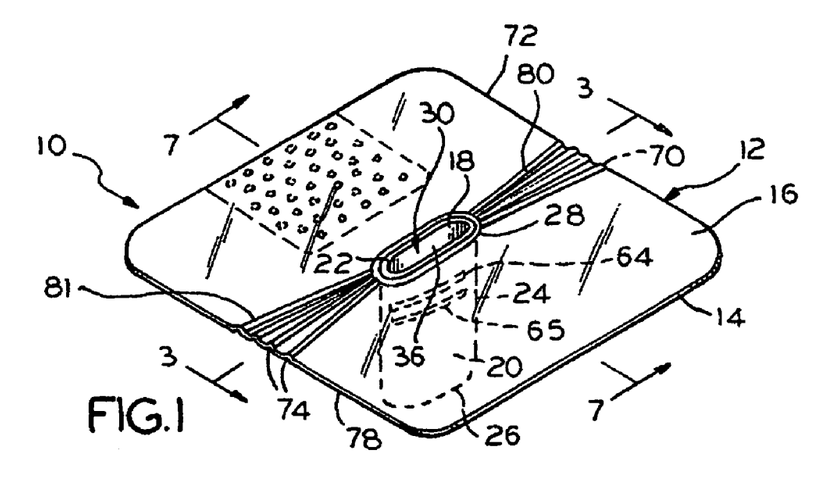
FIG. 1 is a perspective top view of the resuscitator device, embodying the principals of the invention.
Figure 2:
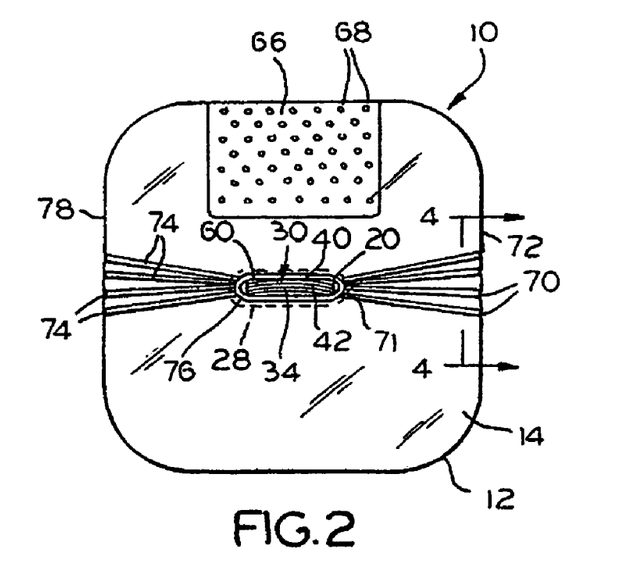
FIG. 2 is a bottom view of the resuscitator device without the safeguard arrangement.

The resuscitator device 10 includes a flexible sheet 12 shown having a substantially square shape, although various other shapes and configurations, may be used, for positioning on the mouth or nose area of the face. The sheet 12 has a bottom side or undersurface 14 (FIG. 2) and a top side or top surface 16 (FIG. 1). An oval mouth opening 18 is centrally formed in the sheet 12.

The sheet 12 is made from a transparent material impermeable by body fluids, moist air and microorganisms. An important characteristic of the material is its ability to conform to the contour of a victim's face. Preferably, the sheet 12 is made of a flexible plastic material such as a polyvinyl chloride (PVC) or similar material such as film-forming thermoplastics including nylon, polyethylene, polypropylene, polyvinyl acetate, soft cellulose acetate etc.

Figure 3:
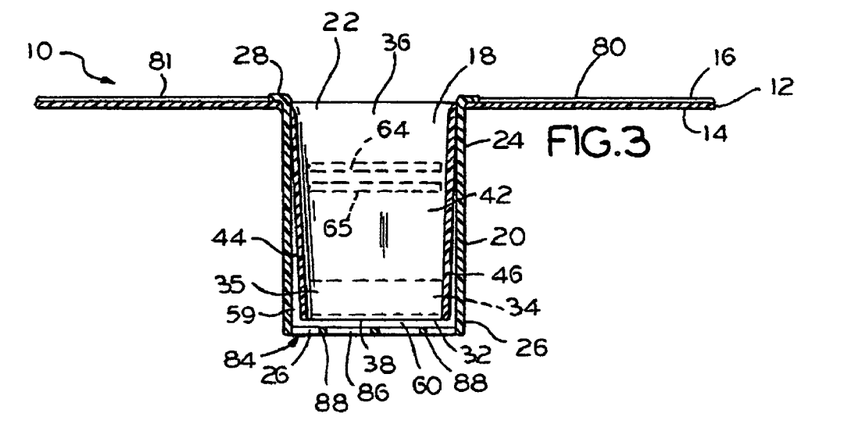
FIG. 3 is a sectional view of the device, taken on the plane of the line 3-3 in FIG. 1, viewed in the direction indicated, and showing the air valve inside the tube.
Figure 4:
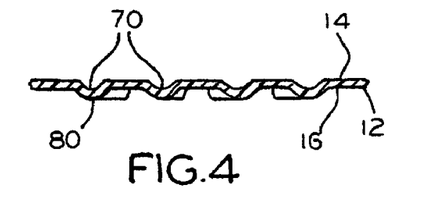
FIG. 4 is a fragmentary sectional view, taken on the plane of the line 4-4 in FIG. 2, viewed in the direction indicated, to show the grooves for providing pathways for air exhaled from the mouth of the person being resuscitated.

A hollow, oval, and rigid plastic tube 20 having a cross-sectional area just slightly less than the mouth opening 18 and that forms a tube passage that is aligned with opening 18 extends downward from the mouth opening 18 along an inner length, as viewed in FIG. 3. The tube 20 includes a first or input end 22, a body portion 24 a second or output end 26, and a length (not labeled) between the first and second ends. The tube 20 has an oblong or oval shape in cross section and an external surface that generally defines the shape. The input end 22 is positioned inside the mouth opening 18.

An oval flange 28 is integrally formed to and surrounds the input end 22 of the tube 20. The flange 28 rests on the top side 16 of the sheet 12 circumscribing the mouth opening 18, so that the tube 20 passes through the opening 18. The combined cross-sectional area of the flange 28 and the body portion 24 of the tube 20 exceeds the cross-sectional area of the opening 18. The flange 28 may be heat bonded or otherwise secured to the top side 16 of the sheet 12. The oval tube 20 and flange 28 are made from a semi-transparent rigid, electrometric material.

A one way, self closing air valve indicated generally by the reference numeral 30 is positioned inside the tube 20. As may be seen from FIG. 10, the valve 30 includes a sleeve 32 and an arcuate spring strip 34 attached to the bottom portion 35 of the sleeve 32. Although the spring 34 is shown attached at the bottom, it may be placed in a variety of positions closer to the air inlet end 36.

Figure 10:
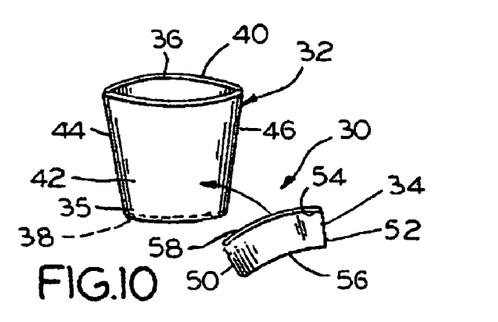
FIG. 10 is a perspective view illustrating the flexible sleeve and the spring strip of the one way air valve spaced from the sleeve prior to being attached thereto.

The sleeve 32 is open at the air inlet end 36 and also at the air outlet end 38, and is constructed from two substantially identical, confronting, thin, flexible walls 40, 42 which are heat sealed along the opposite longitudinal marginal edges 44, 46 thereof. The transverse or horizontal dimensions of the walls 40, 42 progressively decrease and the marginal edges 44, 46 taper inward from the air inlet end 36 to the air outlet end 38. Normally the portions of the confronting walls 40, 42 at the outlet end 38 are flat and close together. The spring strip 34 resiliently forces the portions of the wall adjacent the air outlet end 38 into taut contact. The material for the walls 40, 42 may be a suitable plastic such as a polyvinyl chloride sheet material.

The arcuate spring strip 34 is rigid and flexible, and may be constructed from a rigid polyvinyl chloride sheet or similar material. The spring strip 34 extends across the bottom portion 35 of the sleeve 32 adjacent the outlet end 38, and the side edges 50, 52 of the spring strip 34 are heat sealed to the marginal edges 44, 46 of the walls 40, 42. Similar to the construction of the walls 40, 42, the spring strip tapers inward from the top transverse edge 54 to the bottom transverse edge 56 (FIG. 10).

Figure 5:
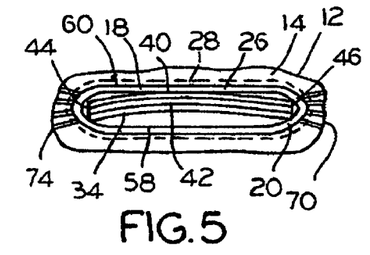
FIG. 5 is a fragmentary enlarged bottom view of the device to illustrate the air valve outlet in a closed condition without the safeguard arrangement.
Figure 6:
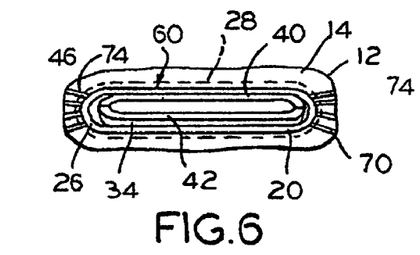
FIG. 6 is a view similar to FIG. 5, and showing the air valve outlet of the device in an open condition for forcing air into the person being resuscitated.
Figures 11A, 11B:
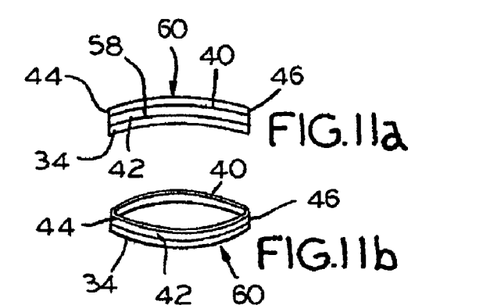
FIG. 11*a* is a schematic bottom view of the valve outlet in a closed-condition.
FIG. 11*b* is a schematic bottom view of the valve outlet in an open condition.

The arcuate spring strip 34 has a convex inner side 58 (FIGS. 5 and 11a). Normally the spring strip 34 resiliently forces the adjacent portions of the valve walls 40, 42 into taut contact with the convex inner side 58, to thereby form an air seal between the walls 40, 42 at the output end 38 of the valve 30.

The air inlet end 36 of the sleeve is opened and heat sealed to the oval inside surface of the tube 20 at the tube input end 22. Therefore, the walls 40, 42 at the valve air inlet 36 are always spread apart. Also, the connection of the air inlet end 36 to the tube 20 seals the device 10 from any air or liquid flow from between the inside surface of the tube and the outside surfaces of the valve walls 40, 42 to the top or rescuer's side 16 of the device 10.

The cooperation of the spring strip 34 with the walls 40, 42 provides an air valve outlet 60. Initially, when no air is forced into the air valve inlet 36, the air valve outlet 60 is closed, since the arcuate spring strip 34 normally maintains the walls 40, 42 in tight frictional contact with each other and wall 42 in taut contact with the convex side 58 of the spring strip 34.

Figure 8:
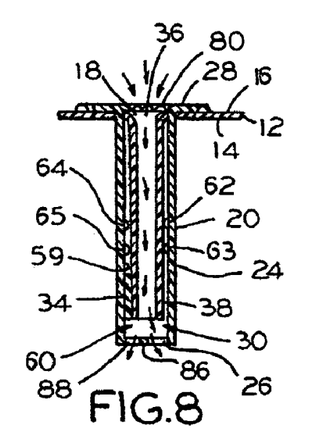
FIG. 8 is a view similar to FIG. 7, but showing the air outlet of the air valve in an open condition.
Figure 9:
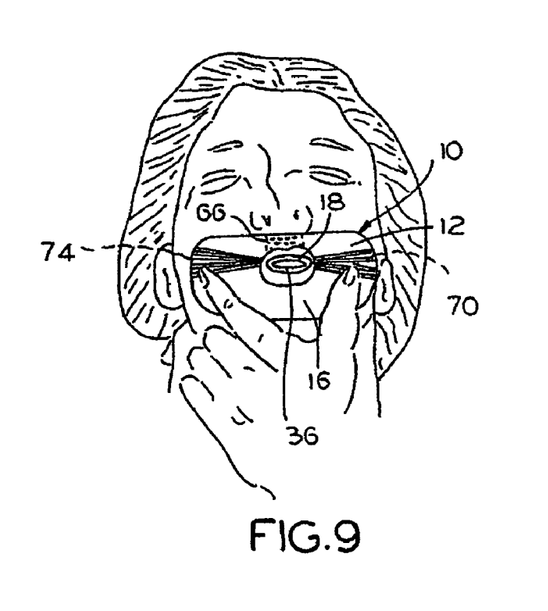
FIG. 9 shows the resuscitator device positioned on the person being resuscitated.

As may be seen from FIG. 8, air forced into the valve inlet 36 causes the air valve outlet 60 to open as the walls 40, 42 spread apart or bow outward from each other, to overcome the resilient closure force of the spring strip 34.

Figure 7:
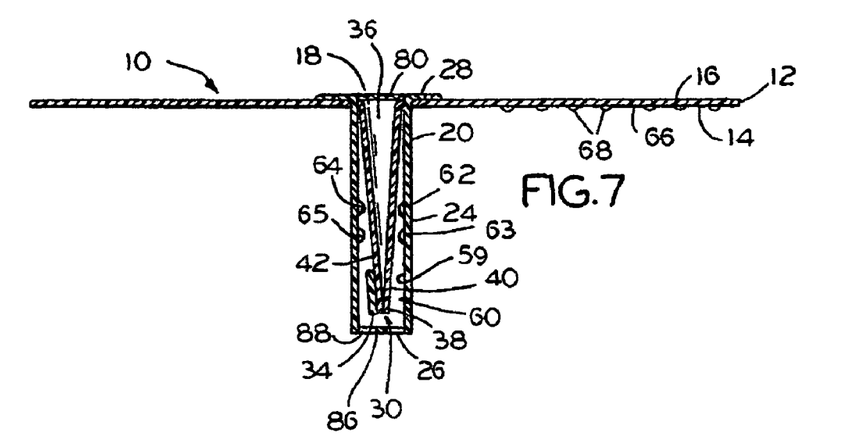
FIG. 7 is a view taken on the plane of the line 7-7 in FIG. 1, viewed in the direction indicated, and showing the air outlet of the air valve in a closed condition.

When air is no longer being forced into the valve inlet 36 the resilient force of the spring strip 34 pulls the adjacent portions of the walls 40, 42 toward each other and into tight frictional contact, thereby returning the air valve outlet 60 to its closed position (FIGS. 7 and 11a).

A pair of ribs 62, 63 are secured to and protrude inward from the inside surface 59 of the tube 20 adjacent to wall 40, and a pair of ribs 64, 65 are secured to and protrude inward from the inside surface 59 adjacent to the wall 42. The ribs 62, 63 prevent the wall 40 from fully contacting the inside surface of the tube 20 and possibly sticking thereto, the effect of which could prevent the air valve 30 from smoothly opening and closing. The ribs are shown extending horizontally as viewed in the drawing, but could extend vertically or in any other suitable manner.

Patch 66 has an irregular non-smooth surface caused by a plurality of small bumps 68. The patch 66 is positioned for contacting the nose or the area of the face adjacent thereto, to prevent any tight contact of the sheet 12 which could prevent the patient from exhaling from the nose upon being resuscitated.

A plurality of grooves or grooves 70 are formed in the bottom side 14 of the sheet 12 and radiate outward from adjacent the edge 71 of the flange 28 to the edge 72 of the sheet 12. Another plurality of grooves 74 are also formed in the bottom side 14 of the sheet 12 and radiate outward from the opposite edge 76 of the flange 28 to the opposite edge 78 of the sheet 12. The formation of the grooves 70, 74 formed on the bottom side 14 of the sheet 12. cause respectfully peaks 80, 81 to be formed on the top side 16. The grooves 70 and 74 provide air pathways to the outside from opposite ends the mouth of the patient, if the patient is trying to or is exhaling when the sheet 12 is in tight contact with the face. In operation, the grooves 70 would be on the left side of the patient's face, and the grooves 74 would be on the right side of the patient's face.

Figure 12:
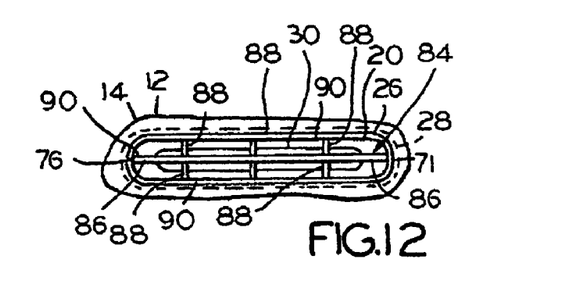
FIG. 12 is a fragmentary view of the device to illustrate the safeguard arrangement secured to the output end of the tube.

Turning now specifically to FIG. 12 of the drawing, it will be seen that a safeguard arrangement indicated generally by the reference numeral 82 is secured to the output end 26 of the tube 20. As shown, the safeguard arrangement 84 includes a longitudinal bar 86 (horizontal as viewed in FIG. 12) and three spaced apart transverse bars 88 (vertical as viewed in FIG. 12) attached to the longitudinal bar 86 and to opposite sides of the output end 26 of the tube 20. Notches 90 are formed inward from the outer end 26 of the tube 20 to receive the ends of the bars 86, 88 and thereafter heat bonded or otherwise secured thereto. Similarly notches 92 are formed in the longitudinal bar 86 to support the bars 88, and thereafter the bars 88 are heat bonded or otherwise secured thereto.

The safeguard arrangement prevents the possibility of the tongue of the victim from inhibiting the operation of the valve 30 on the inside of the tube 20. Various configurations for the safeguard arrangement 84 are contemplated provided that it affords a screen or wall effect without preventing the desired air flow from the valve outlet 60 into the victim's mouth.

When resuscitating a victim with the device 10 or practicing the technique, the mouth of the victim is opened and the mouth is cleared of any obstruction; and the tongue is observed to be sure it is positioned in the lower part of the mouth. The tube 20 is inserted into the mouth of the victim, so that the bottom side 14 of the sheet 12 contacts the face of the victim and the top side 16 is opposed to the face of the rescuer. A deep breath is taken and the lips of the rescuer surrounds the mouth opening 18 and is pressed against the lips of the victim with the sheet 12 therebetween, thereby creating an air seal between the lips. The rescuer may brace the inner portions of the lips against the flange 28 to develop greater pressure.

Then the deep breath is evenly exhaled under pressure into the valve inlet 36 via the mouth opening. The exhaled air causes the walls 40, 42 to spread apart and has sufficient force to overcome the resilient closing force of the spring strip 34, thereby opening the air outlet valve 60 to discharge the exhaled air into the mouth of the victim via the tube output end 26. After the deep breath has been fully exhaled, the spring strip 34 closes the air outlet valve 60, and prevents a reverse flow of air and/or liquid from the victim to the rescuer. The rescuer takes another deep breath and repeats the resuscitation process, for delivering another large volume of air to the lungs of the victim. The shield afforded by the impermeable, flexible and contour forming sheet 12 and the instant acting self closing one way valve 30 provide a positive barrier separating the rescuer from the victim, which enables the rescuer to fully concentrate on the resuscitation of the victim without concern that he or she may be contracting a deathly virus or disease.

Thus, after the device 10 is in place: tube 20 is inserted in victim's mouth and sheet 12 completely covers the victim's mouth and lips; the sheet 12 is flush against the victim's face; nostrils are pinched closed; and C.P.R. approved techniques may be used.

Figure 13:
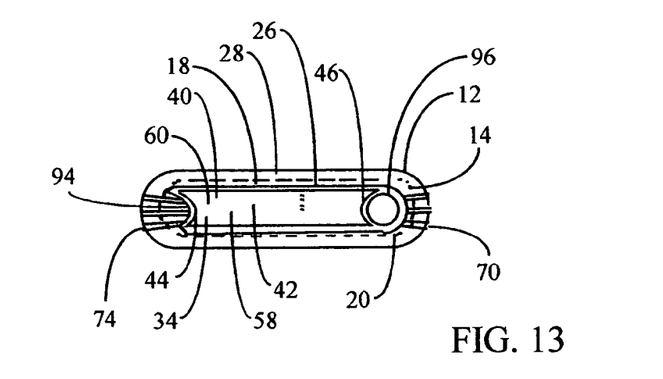
FIG. 13 is a fragmentary view of the device to illustrate side exhalation channels.

FIG. 13 is similar to FIG. 5 but now showing tube 20, previously drawn as an oval, with at least one exhalation channel 94. While the tube has been shown in previous embodiments as having an oval or oblong exterior shape, having curved long oppositely facing wall portions, and first and second end walls at opposite ends of the long wall portions (i.e., at opposite ends of a wide dimension of the tube), in FIG. 13 a channel 94 is cut into or formed at one end of the oval shape. Channel 94 runs from a first channel end at bottom side or undersurface 14 of sheet 12 along the length of tube 20 to a second outlet end 26. The first end, in some embodiments, may be truncated a distance from sheet 12 sufficient to extend into the victim's mouth beyond their lips. As shown, channel 94 is positioned so as to fit adjacent to a corner of a victim's mouth. While the victim's lips may tightly wrap around the oval shaped portion of tube 20, channel 94 will naturally remain open.

While valve 30 prevents air or fluids from passing through tube, channel 94 forms a passageway to allow victim exhalation. In some embodiments, channel 94 is connected to or opens into groove 70 so air can pass under sheet 12 and exit. In at least some embodiments, channel 94 also allows saliva or other fluids in the mouth to flow out without resuscitator device 10 having to be removed.

Other features to prevent the lips from clogging channel 94 are contemplated. For example bars placed where the victim's lips make contact with tube 20 may serve a similar purpose as channel 94.

Referring again to FIG. 13, in another embodiment, a channel 96 may be enclosed along part of its length, for example in the area covered by the victim's lips. The second end of channel 96 within the victim's mouth is open and the first end adjacent sheet 12 is open to grooves 70. This allows free communication of air in the victim's mouth with the outside when the rescuer is not pressing his lips against the victim's face during mouth-to-mouth resuscitation and prevents the resuscitation device 10 from being dislodged should the victim start to breath on their own or during chest compressions.

Figure 14:
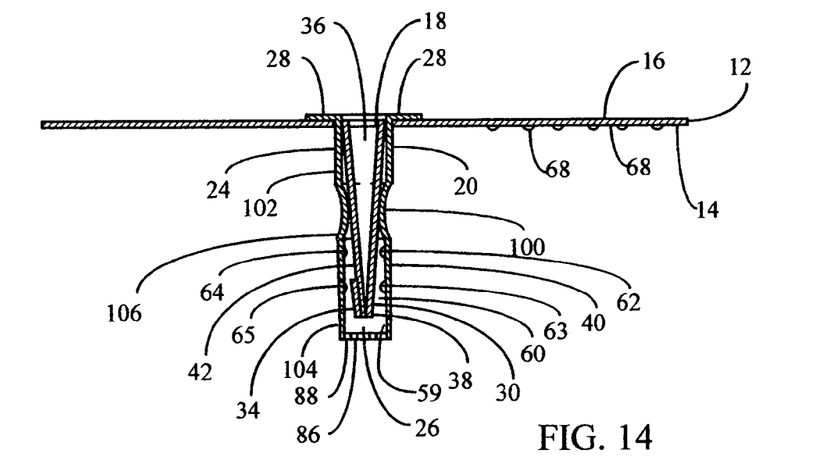
FIG. 14 is a view similar to FIG. 7, but showing a teeth guard along the tube extending into the victim's mouth.

FIG. 14 shows resuscitator device 10 with two victim teeth recesses 100, shown as concave or recessed sections running along opposite sides of oval tube 20. The recesses 100 are aligned so as to be substantially perpendicular to the tube length. Recesses 100 divide the tube body portion 24 into an upper section 102 and a lower section 104. Upper section 102 extends along tube 20 a distance sufficient to accommodate the victim's lips so that the victim's teeth naturally rest in teeth recesses 100. For example upper section can be ¼" to ¾" long.

Figure 15:
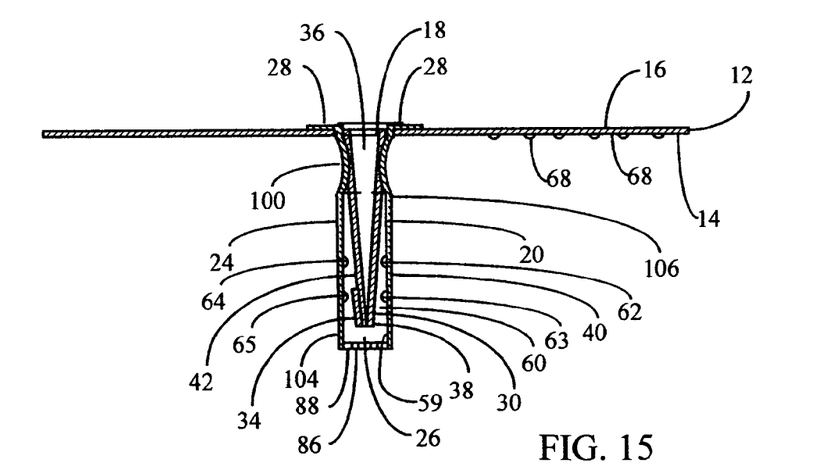
FIG. 15 is a view similar to FIG. 14, showing an alternate position of a teeth guard along the tube extending into the victim's mouth.

In another embodiment recesses 100 are formed adjacent to sheet 12 without upper section 102 (see FIG. 15). To secure victim's teeth, recesses 100 can extend along body portion 24 ⅜" to 1" from air inlet end 36.

When tube 20 is placed in the victim's mouth, recesses 100 allow the victim's teeth and jaw to assume a more natural configuration than when a tube without recesses 100 is present. Recesses 100 also helps to secure resuscitator device 10 in a victim's mouth by resistance of the victim's teeth along lower edge 106 of recesses 100, for example the edge nearest to outlet end 38. In this manner device 10 is easily pushed out by force of the motion of the victim when teeth are parted and removed from recesses 100.

Figure 16:
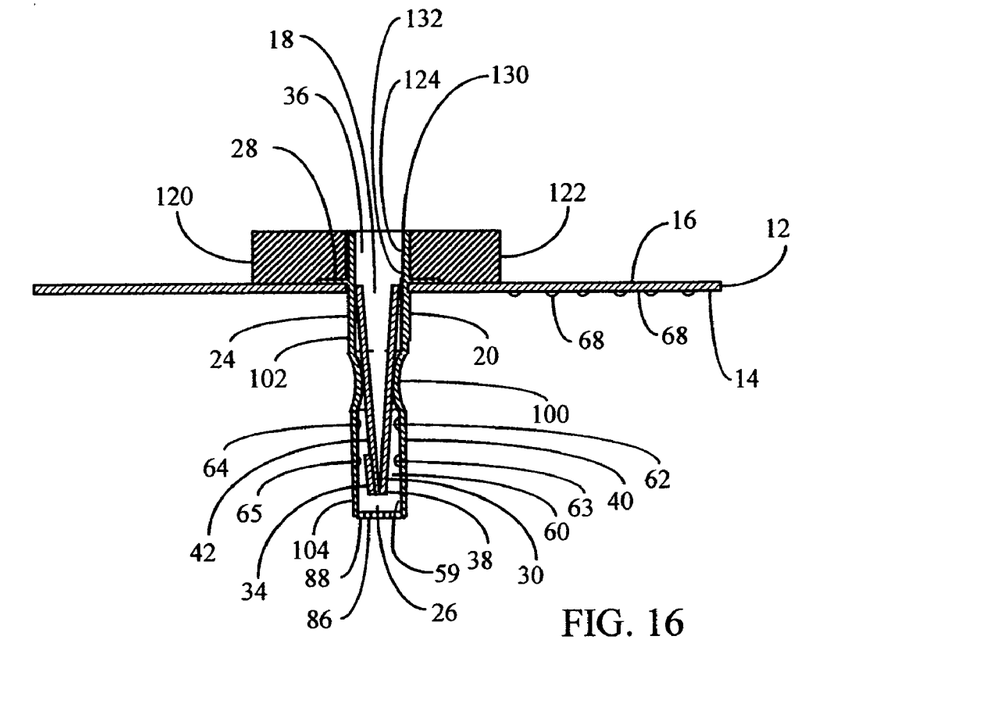
FIG. 16 is a view similar to FIG. 14, but now showing an alternate teeth guard positioned extending into the rescuer's mouth.
Figure 17:
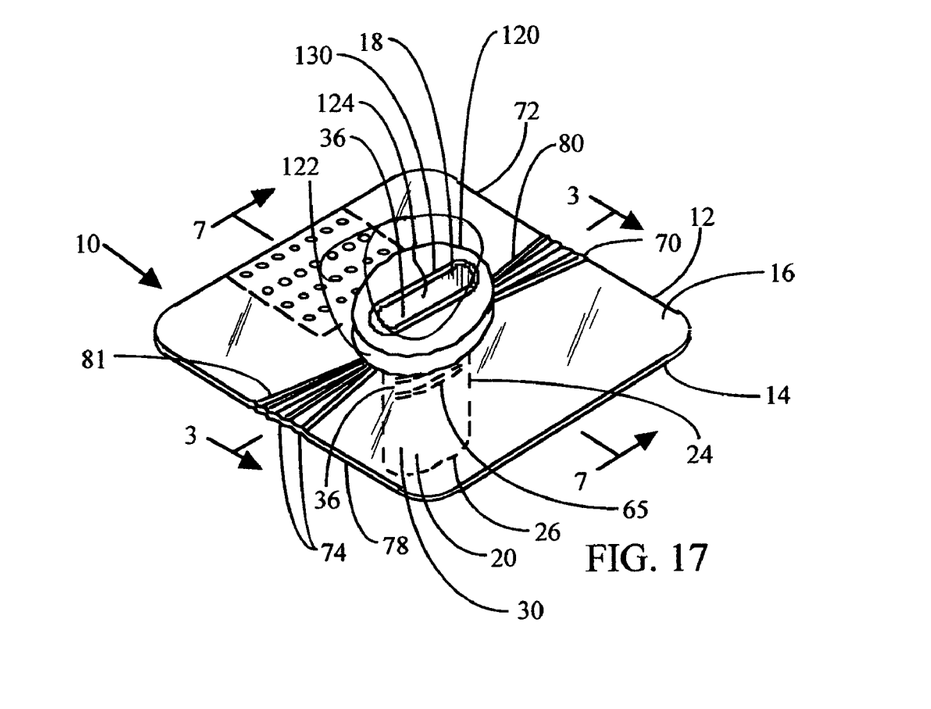
FIG. 17 is a view similar to FIG. 1, but now showing a teeth guard extending into the rescuer's mouth.

Referring to FIGS. 16 and 17, in another embodiment, a victim's and a rescuer's teeth are protected by a guard 120. In FIGS. 16 and 17, guard 120 is placed on the top side 16 of sheet 12 and made of a force absorbing resilient and flexible material such as, for instance, a low durometer silicone plastic, a synthetic rubber or a closed cell foam. The rescuer places her lips around perimeter 122 of guard 120 and presses them against sheet 12 to form a tight seal between undersurface 14 and the victim's lips. Should the victim suddenly move when the rescuer is performing mouth-to-mouth resuscitation, guard 120 absorbs the force of such movement and prevents the victim's and rescuer's teeth from damaging each other.

To prevent guard 120 from deforming during mouth-to-mouth resuscitation, tube 20 can extend beyond top side or surface 16 to form an exterior section 124 where the tube has a first tube portion 124 on a top surface side and a second tube portion 24 on an undersurface side. In the FIG. 16 embodiment, a surface of guard 120 that faces away from sheet 12 is flush with a first end 36 of tube portion 124. Section 124 extends along an exterior length from an open extended first end 130 to mouth opening end 132 in communication with portion 24. It is contemplated that while guard 120 is shown in vertical section as having a rectangular shape, guard 120 may have a variety of other shapes such as, for instance, a triangular cross-sectional shape sloping away from air inlet 36 towards the perimeter of sheet 12. Oval, or other angular shapes can be used to assist the rescuer in creating an air seal between sheet 12 and the face of the victim.

Guard 120 can be used with or without recesses 100.

Figure 18:
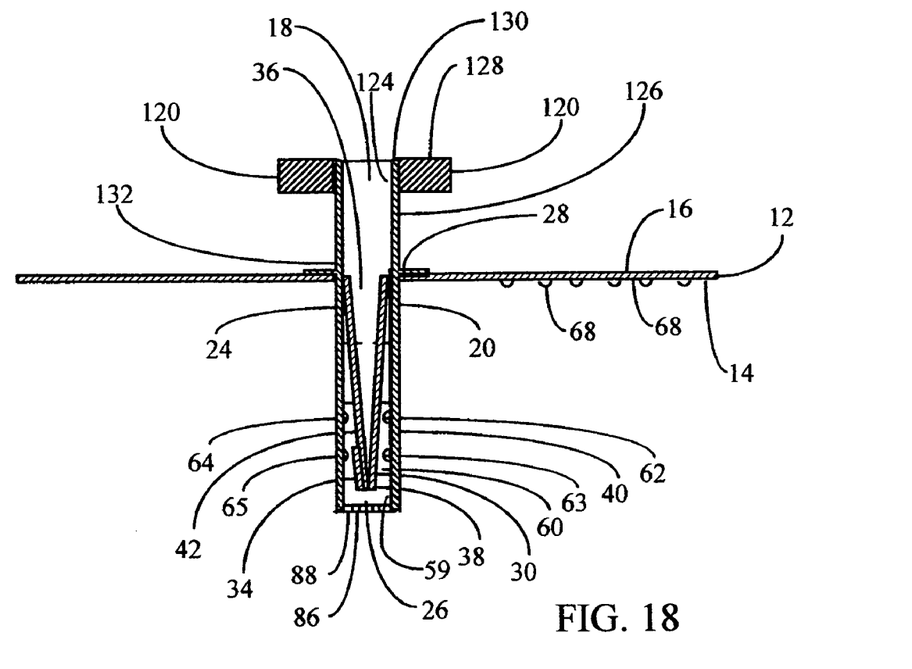
FIG. 18 is a view similar to FIG. 7, but now showing another alternate teeth guard extending into the rescuer's mouth.

Guard 120 can also be positioned so it is not in contact with sheet 12 as shown in FIG. 18. In this embodiment, guard 120 is raised above sheet, for example, by ¼" to ¾", allowing a portion 126 of section 124 to be exposed. The rescuer now places their lips around portion 126 and in contact with sheet 12 to create a tight seal between bottom side 14 and the victim's lips. The rescuer's teeth are placed above top surface 128 of guard 120 on the air inlet side of guard 120.

Figure 19:
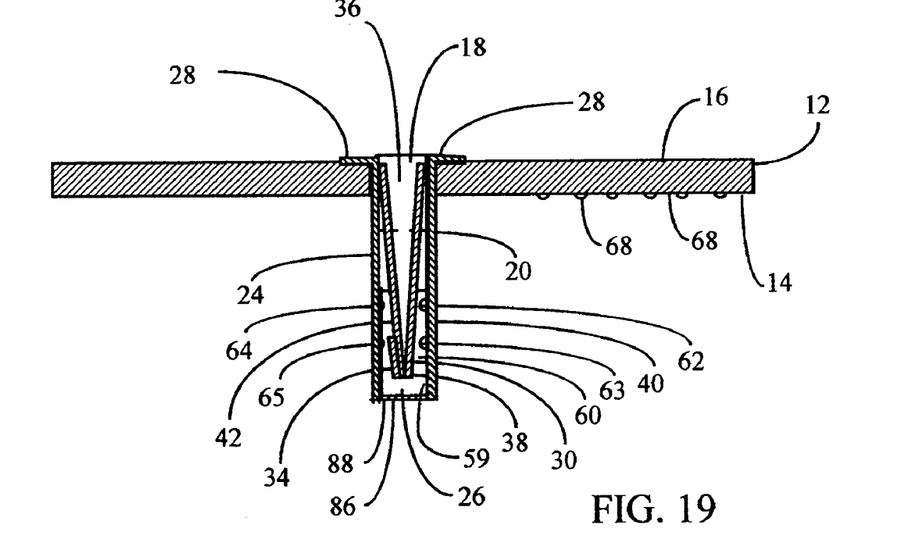
FIG. 19 is a view similar to FIG. 8, showing another alternate teeth guard placed between the lips of the rescuer and the victim.

In another embodiment sheet 12 can be formed using a thick sheet of shock absorbing material that is impermeable by body fluids, moist air and microorganisms to act as a teeth guard (see FIG. 19). It is contemplated that in this form, sheet will be at least ¼" thick in the area adjacent to air inlet 36 and may be thinner toward the perimeter of sheet 12.

Figure 20A:
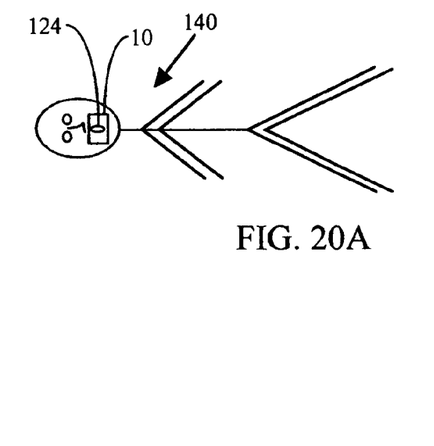
FIG. 20A shows a resuscitator device placed in a victim's mouth where the tube that is inserted into the victim's mouth is reshaped as it projects into the rescuer's mouth.
Figure 20B:
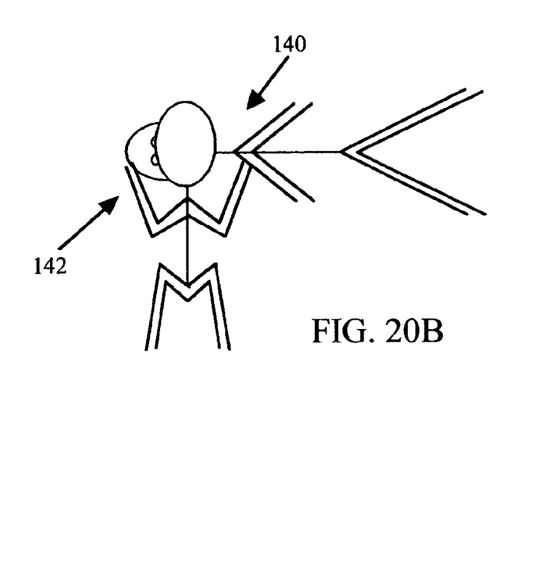
FIG. 20B shows the normal position of a rescuer and victim when mouth-to-mouth resuscitation is performed.
Figure 21:
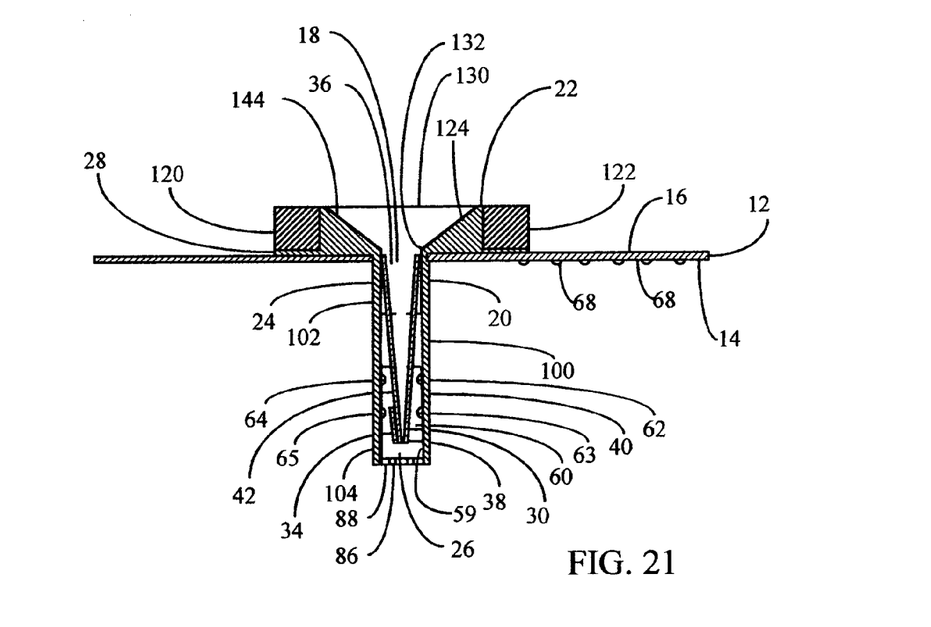
FIG. 21 is a view taken on the plane of the line 21-21 in FIG. 22, viewed in the direction indicated, and showing a tube extending into the victim's mouth changing in shape as it extends and enters the rescuer's mouth.
Figure 22:
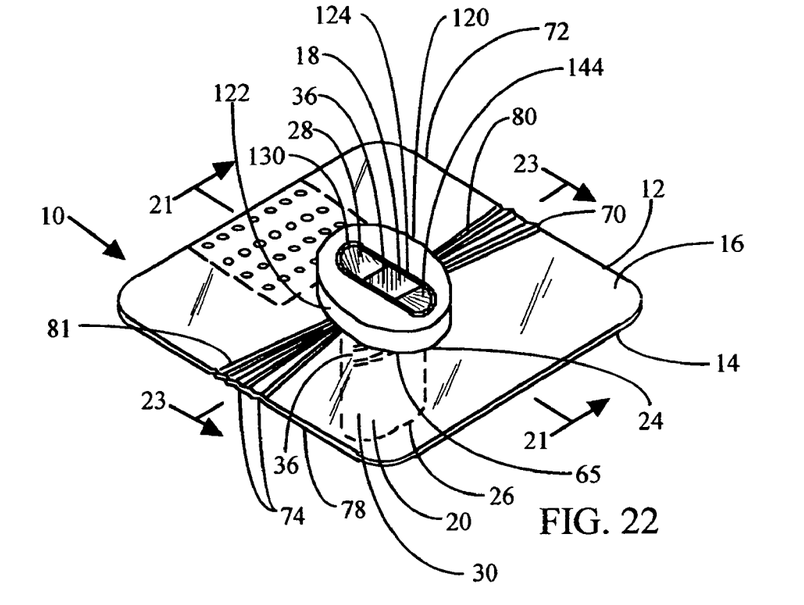
FIG. 22 is a perspective top view of the resuscitator device, similar to FIG. 1, showing a tube that is placed in the victim's mouth that changes in shape as it enters the rescuer's mouth.

Another embodiment is shown in FIGS. 20A, 20B and 21 to 23. In mouth-to-mouth resuscitation, a victim 140 and a rescuer 142 are oriented approximately so they are perpendicular to each other (see FIG. 20B). As before, resuscitator device 10 is shown inserted in the mouth of victim 140 so sheet 12 covers the victim's mouth (FIG. 20A). As before, tube 20 is placed between the teeth of the victim 140, but section 124 is now shaped so that it no longer is a direct continuation of the shape of body portion 24. In FIGS. 20A and 22, section 124 is shown as an oval, but now rotated at least 45° and in some cases 90° to body portion 24 oriented to match the natural position of the mouth of rescuer 142. FIG. 22 shows section 124 rotated by 90 degrees from body portion 24.

It is also anticipated that section 124 may rotate around mouth opening 18 about a mouth opening axis (not labeled) perpendicular to top surface 16 of sheet 12 (i.e., substantially perpendicular to the portion of the sheet adjacent the mouth opening). This allows exterior section 124 to be conveniently arranged for storage and/or to accommodate different rescuer/victim positions. For instance, when section 124 and body portion 24 are similarly shaped, section 124 and portion 24 can be arranged to be parallel. When the device is to be used, section 124 can be rotated so as to be in a more convenient position for alignment with the rescuer's mouth.

Figure 23:
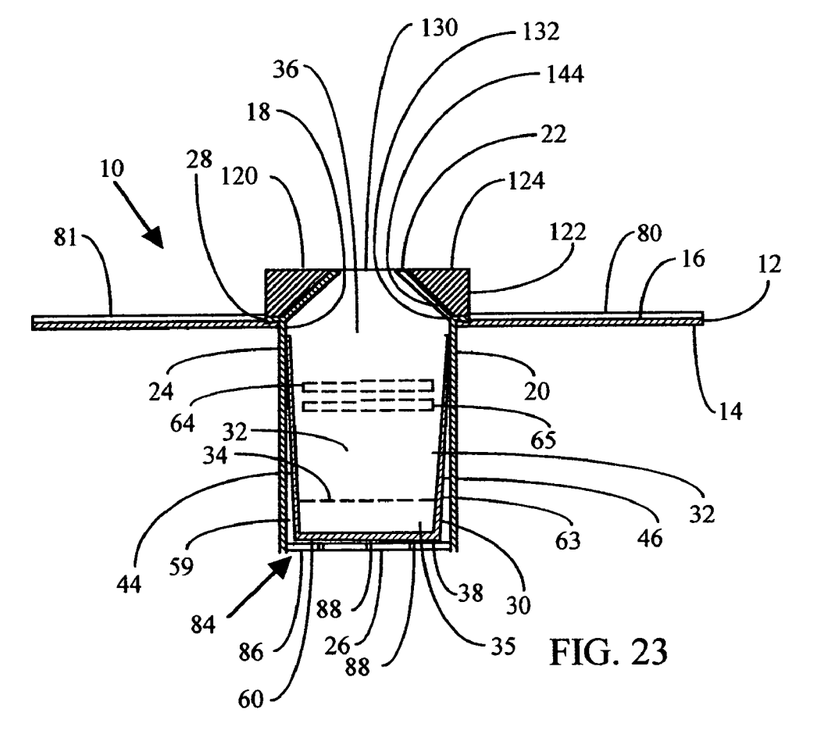
FIG. 23 is a view taken on the plane of the line 23-23 in FIG. 22, viewed in the direction indicated, and showing a tube extending into the victim's mouth changing in shape as it extends and enters the rescuer's mouth.

Wall 144 of section 124 changes in shape to match the shape of body portion 24 as shown in FIGS. 21 and 23. Teeth guard 120 surrounds section 124 to provide protection to the teeth of the rescuer 142 and the victim 140. While the surfaces that form section 124 are shown as flat, the surfaces may be curved from body sheet 12 to input end 22. While shown as an oval in cross section, open extended end 130 may have a circular shape, provided that it allows at least 2 cm² of free flow area for air to pass through into tube 20 and into victim 140.

As before, rescuer 142 firmly places his lips around guard 120 forcing sheet 12 to make a tight seal with the mouth and surrounding face of the victim 140. By the rescuer 142 placing his teeth behind guard 120, the teeth of rescuer 132 and victim 140 are protected from making contact with each other.

It is anticipated that recesses 100 and guard 120 can be combined with channels 94 or 96 to form a resuscitator device 10 that both facilitates easy exhalation and protects teeth.

Various modifications of the invention of a mouth-to-mouth resuscitator device described herein are within the spirit and scope of the invention, the scope of which is limited solely and defined by the appended claims. For example, while guard member 120 (see FIG. 17) is shown generally as a single doughnut shaped member, member 120 may comprise two or more members that are supported by either sheet 12 or a first end of the tube. In addition, while channel 94 (see FIG. 13) is described as opening adjacent the undersurface of sheet 12, channel 94 may extend along the undersurface of sheet 12 to a lateral edge thereof. Moreover, the number of channels 94, 96 may be greater than two in at least some embodiments. Furthermore, either of the first or second portions 124 or 24, respectively, in FIGS. 21-23 may rotate with respect to sheet 12 about the mouth opening axis.

What is claimed is:

1. A mouth to mouth resuscitator device for use by a rescuer for resuscitating a victim, the device comprising:
    a sheet of flexible material having a top surface and an undersurface, the sheet forming a mouth opening;
    a hollow substantially rigid tube having an external surface, a first end, a second end and a tube length between the first and second ends, a tube passage aligned at least in part with the mouth opening, the tube having a major and minor cross-sectional dimension and extending from the undersurface of the sheet to the second end;
    a self closing one-way valve located within the tube passage to restrict flow from the second end to the first end of the tube and to allow flow from the first end to the second end when a rescuer exhales air into the mouth opening; and
    at least a first resilient and flexible tooth guard member having a major and minor cross-sectional dimension that surrounds at least a portion of the mouth opening on the top surface side of the sheet, the at least one guard member supported by at least one of a portion of the tube and the sheet for absorbing force, wherein the major cross-sectional dimensions are misaligned.

2. The device of claim 1 wherein the guard member is supported by a portion of the external surface of the tube.

3. The device of claim 2 wherein the tube extends through the sheet to the first end that is spaced apart from the top surface and wherein the at least one guard member surrounds the external surface of the tube adjacent the first end of the tube.

4. The device of claim 3 wherein the at least one guard member contacts the top surface of the sheet and includes a surface that is substantially flush with the first end of the tube.

5. The device of claim 4 wherein the at least one guard member has a thickness between the top surface of the sheet and the surface that is substantially flush with the first end of the tube that is at least ¼th of an inch.

6. The device of claim 3 wherein the guard member is spaced apart form the top surface of the sheet.

7. The device of claim 6 wherein the separation between the top surface of the sheet and the guard member is at least ¼th of an inch.

8. The device of claim 1 wherein the first end of the tube is substantially oval in cross section.

9. The device of claim 1 wherein the device is positionable with the second end in the victim's mouth and the sheet coving a portion of the victim's face such that when the rescuer's lips surround the at least one guard member with the guard member positioned between the rescuer's teeth and the sheet, as the rescuer's lips are pressed against the sheet, an air seal is created between the device and the victim.

10. The device of claim 1, wherein the mouth opening is oval shaped and the external surface of the tube proximate the undersurface of the sheet is substantially oval in cross section to force the lips and teeth of the victim slightly apart thereby enabling the lips of the rescuer to easily make a tight air seal with the victim's mouth when the sheet is therebetween.

11. A mouth to mouth resuscitator device for use by a rescuer for resuscitating a victim, the device comprising:
    a sheet of flexible material having a top side for contacting the rescuer and an undersurface side for contacting the victim, the sheet forming a mouth opening;
    a hollow substantially rigid tube having an external surface, a first end, a second end and a tube length between the first and second ends, a tube passage aligned at least in part with the mouth opening, the tube extending from the undersurface of the sheet to the second end;
    a self closing one-way valve located within the tube passage to restrict flow from the second end to the first end of the tube and to allow flow from the first end to the second end when a rescuer exhales air into the mouth opening; and
    a first channel supported by at least one of the tube and the sheet that extends along at least a portion of the tube length, the channel having first and second channel ends, the first end of the channel opening on the undersurface side of the sheet and the second end of the channel proximate the second end of the tube.

12. The device of claim 11 wherein the external surface of the tube is oblong in cross section having first and second oppositely facing side walls at opposite ends of a wide dimension and wherein the tube forms the first channel in the first side wall.

13. The device of claim 12 wherein tube further forms a second channel in the second side wall.

14. The device of claim 11 wherein, when the second end of the tube is in a victim's mouth, the second end of the channel is in the victim's mouth.

15. The device of claim 11 wherein the undersurface of the sheet forms at least one air groove extending from adjacent the mouth opening to an outer edge of the sheet and wherein the second end of the channel opens into the at least one groove.

16. The device of claim 11 wherein the channel is closed along at least a portion of a channel length between the first and second channel ends.

17. A mouth to mouth resuscitator device for use by a rescuer for resuscitating a victim, the device comprising:
- a sheet of flexible material having a top side for contacting the rescuer and an undersurface side for contacting the victim, the sheet forming a mouth opening;
- a hollow substantially rigid tube having an external surface, a first end, a second end and a tube length between the first and second ends, a tube passage aligned at least in part with the mouth opening, the tube including a first tube portion extending from the top surface to the first end and a second tube portion extending from the undersurface of the sheet to the second end where the first and second ends are spaced apart from the top and undersurfaces of the sheet, respectively; and
- a self closing one-way valve located within the tube passage to restrict flow from the second end to the first end of the tube and to allow flow from the first end to the second end when a rescuer exhales air into the mouth opening;

wherein the first tube section is oblong in cross section perpendicular to the tube length and has a first wide cross sectional dimension and the second tube section is oblong in cross section perpendicular to the tube length and has a second wide cross sectional dimension and wherein the first and second wide dimensions are misaligned.

18. The device of claim 17 wherein the misalignment is at least 45 degrees.

19. The device of claim 18 wherein the misalignment is 90 degrees.

20. The device of claim 17 wherein each of the first and second tube portions have oval cross sectional shapes.

21. The device of claim 17 further including at least one resilient and flexible guard member supported by and that at least in part surrounds a portion of the external surface of the first tube portion.

22. The device of claim 17 where at least one of the first and second tube portions is connected to the sheet to rotate around the mouth opening about a mouth opening axis that is substantially perpendicular to the portion of the sheet adjacent the mouth opening.

* * * * *